United States Patent [19]
Rabinovich et al.

[11] Patent Number: 5,861,398
[45] Date of Patent: Jan. 19, 1999

[54] BENZOPERIMIDINE-CARBOXYLIC ACIDS AND DERIVATIVES THEREOF

[75] Inventors: Aleksandr K. Rabinovich, La Jolla; Dale S. Dhanoa, Del Mar; David R. Luthin, San Diego; Richard A. Bychowski, Cardiff; Dilip R. Bhumralkar, San Diego, all of Calif.

[73] Assignee: Alanex Corporation, San Diego, Calif.

[21] Appl. No.: 703,025

[22] Filed: Aug. 26, 1996

[51] Int. Cl.$^6$ .................. C07D 403/02; A61K 31/495
[52] U.S. Cl. .............................. 514/250; 544/245
[58] Field of Search .................... 544/245, 248; 514/250, 257

[56] References Cited

U.S. PATENT DOCUMENTS

| | | | |
|---|---|---|---|
| 3,939,162 | 2/1976 | Elser et al. | 260/256.4 |
| 4,001,170 | 1/1977 | Wick | 260/40 P |
| 4,927,820 | 5/1990 | Shutske et al. | 514/229 |
| 5,063,245 | 11/1991 | Abreu et al. | 514/404 |
| 5,441,975 | 8/1995 | Lee et al. | 514/406 |

FOREIGN PATENT DOCUMENTS

| | | |
|---|---|---|
| 0 576 350 A1 | 10/1993 | European Pat. Off. . |
| WO 94/13644 | 6/1994 | WIPO . |
| WO 94/13661 | 6/1994 | WIPO . |
| WO 94/13676 | 6/1994 | WIPO . |
| WO 94/13677 | 6/1994 | WIPO . |
| WO 95/10506 | 4/1995 | WIPO . |

OTHER PUBLICATIONS

Berge, S., et al. (1977) Pharmaceutical salts. Journal of Pharmaceutical Sciences 66(1):1–18.

Brown, M., et al. (1982) Corticotropin–releasing factor (CRF): effects on the sympathetic nervous system (SNS), vasopressin release and cardiovascular regulation. Endocrinology 110:225.

Brown, M., et al. (1985) Corticotropin–releasing factor: effects on the automatic nervous system and visceral systems. Federation Proceedings 44(1):243–248.

Brown, M., et al. (1981) Corticotropin–releasing factor: effects on the sympathetic nervous system and oxygen consumption, Life Sciences 30:207–210.

Chang, C., et al. (1993) Identification of a seven transmembrane helix receptor for corticotropin–releasing factor and sauvagine in mammalian brain. Neuron 11:1187–1195.

Dunn, A., et al. (1990) Physiological and behavioral responses to corticotropin–releasing factor administration: is CRF a mediator of anxiety or stress responses? Brain Research Review 15:71–100.

Ehlers, C.L., et al. (1983) Corticotropin releasing factor produces increases in brain excitability and convulsive seizures in rats. Brain Research 278:332–336.

Fisher, L., et al. (1991) Differential antagonist activity of α–helical corticotropin–releasing factor$_{9-41}$ in three bioassay systems. Endocrinology 129(3):1312–1316.

Furutani, Y., et al. (1983) Cloning and sequence analysis of cDNA for ovine corticotropin–releasing factor precursor. Nature 301(10):537–540.

Harris, G.W. (1948) Neural control of the pituitary gland. Physiological Reviews 28(2):139–179.

Heinrichs, S., et al. (1995) The role of CRF in behavioral aspects of stress. Ann. NY. Acad. Sci. 771:92–104.

Irwin, M., et al. (1988) CRF activates autonomic nervous system and reduces natural killer cytotoxicity. Neural Control of Immune Function 255:R744–R747.

Kishimoto, T., et al. (1995) A sauvagine/corticotropin–releasing factor receptor expressed in heart and skeletal muscle. Proc. Natl. Acad. Sci. 92:1108–1112.

Koob, G., et al. (1985) Corticotropin–releasing factor and behavior. Federation Proceedings 44(1):259–263.

Levine, A.S., et al. (1983) Effect of centrally administered corticotropin releasing factor (CRF) on multiple feeding paradigms. Neuropharmacology 22(3A) 337–339.

Rivier, J., et al. (1983) Characterization of rat hypothalamic corticotropin–releasing factor. Proc. Natl. Acad. Sci. 80:4851–4855.

Sirinathsinghji, D., et al. (1983) Corticotropin–releasing factor is a potent inhibitor of sexual receptivity in the female rat. Nature 305:232–235.

Spiess, J., et al. (1981) Primary structure of corticotropin–releasing factor from ovinge hypothalamus. Proc Natl. Acad. Sci. 78(10):6517–6521.

Sutton, R., et al. (1982) Corticotropin releasing factor produces behavioural activation in rats. Nature 297:331–333.

Vale, W., et al. (1981) Characterization of a 41–residue ovine hypothalamic peptide that stimulates secretion of corticotropin and β–endorphin. Science 213:1394–1397.

(List continued on next page.)

*Primary Examiner*—Mukund J. Shah
*Assistant Examiner*—Deepak R. Rao

[57] ABSTRACT

Benzo(e)perimidine-4-carboxamide derivatives of general structural formula I

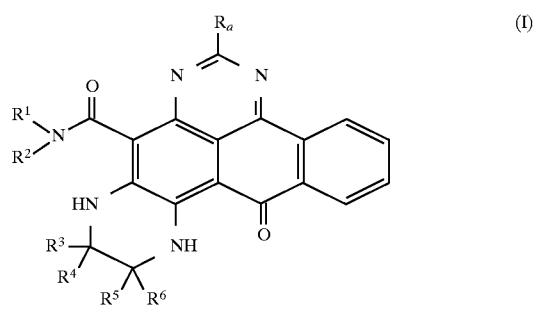

(where $R_a$, $R^1$, $R^2$, $R^3$, $R^4$, $R^5$, and $R^6$ are as defined in the specification) have activity for receptors of corticotropin releasing factor (CRF). The compounds are useful in treating stress-related diseases, cardiovascular, neurological and psychiatric disorders including anxiety, depression, eating disorders, anorexia nervosa, superanuclear palsy, irritable bowel syndrome, gastrointestinal diseases, immune suppression, inflammatory disorders, drug and alcohol withdrawal symptoms, drug addiction, Alzheimer's disease or fertility disorders.

23 Claims, No Drawings

OTHER PUBLICATIONS

Williams, C., et al. (1987) Corticotropin–releasing factor directly mediates colonic responses to stress. Am J. Physiol 253:G582–G586.

Holsboer et al., The role of corticotropin–releasing hormone in the pathogenesis of Cushing's disease, Progress in Brain Research, vol. 93, Ch. 27, pp. 385–417, 1992.

Leonard et al., Stress and the Immune System in the Etiology of Anxiety and Depression, Pharmacology Biochemistry and Behaviour, vol. 54, No. 1, pp. 299–303, 1996.

Weiss et al., Depression and Anxiety, Brain Research Bulletin, vol. 35, No. 5/6, pp. 561–572, 1994.

DeSouza, CRF Receptors, Psychoneuroendocrinology, vol. 20, No. 8, pp. 789–819, 1995.

Coplan et al., Persistent elevations of cerebrospinal fluid concentrations of CRF, Proc. Natl. Acad. Sci. USA, vol. 93, pp. 1619–1623, Feb. 1996.

Damasio, Alzheimer's Disease and Related Demetias, Cecil Textbook of Medicine, 20th Edition, vol. 2, pp. 1992–1994, 1996.

Zaitsev et al., Chem. abstr. 125:142023, 1996.

Hirose, Chem. abstr. 123:127575, 1995.

Antonini et al., Chem. abstr. 118:182772, 1993.

Stefanska et al., Chem. abstr. 118:38872, 1993.

Moriga et al., Chem. abstr. 86:114448, 1977.

Popov et al., Chem. abstr. 83:10137, 1975.

Saenger et al., Chem. abstr. 80:15740, 1974.

BENZOPERIMIDINE-CARBOXYLIC ACIDS AND DERIVATIVES THEREOF

FIELD OF THE INVENTION

This invention relates to non-peptidic antagonists of corticotropin releasing factor receptors. It relates particularly to perimidine-based compounds having CRF antagonist activity.

BACKGROUND OF THE INVENTION

CRF is a 41-amino acid linear peptide isolated from ovine hypothalmia. CRF plays a crucial role in integrating the body's overall response to stress. Although the existence of CRF was postulated more than thirty years ago (G. W. Harris, *Physiol. Rev.* 28:139), its purification and sequencing was reported in 1981 (W. Vale et al., *Science*, 213, 1394 (1981); J. Spiess et al. *Proc. Natl. Acad. Sci., U.S.A.*, 78, 6517 (1981)). Shortly thereafter the sequences of human and rat CRF were determined and these were found to be the same, but differed from ovine CRF (oCRF) in 7 of the 41 amino acid residues (J. Rivier et al. *Proc. Natl. Acad. Sci., U.S.A.*, 80, 4851 (1983)); Furutani et al. *Nature*, 301, 537 (1983). CRF produces profound alterations in behavioral and autonomic nervous system functions (M. R. Brown and L. A. Fisher, *Fed. Proc.*, 44, 243 (1985); G. F. Koob, F. E. Bloom, *Fed. Proc.*, 44, 259 (1985)). Upon direct administration into the brain, CRF initiates behavioral, physiological and endocrine responses that are essentially identical to those observed when animals are exposed to stressful environment. When given, for example, by intracerebroventricular (icv) injection, CRF induces behavioral activation (R. E. Sutton et al. *Nature* 297, 331 (1982)), it produces a long-lasting activation of the electroencephalogram (C. L. Ehlers, et al. *Brain Res.* 278, 332 (1983)), stimulates the sympathoadrenomodullary pathway (M. R. Brown et al. *Endocrinology* 110, 928 (1982)), increases heart rate, raises blood pressure and increases oxygen consumption (L. A. Fisher et al. *Endocrinology* 1 10, 2222 (1982)), alters gastrointestinal activity (M. R. Brown et al. *Life Sciences* 30, 207 (1982), suppresses food intake (C. L. Williams et al. *Am. J Physiol,* 253, G582 (1987) and sexual behavior (A. S. Levine et al. *Neuropharmacology,* 22, 337 (1983)), and affects immune function (D. J. S. Sirinathsinghji et al. *Nature,* 305, 232 (1983); M. Irwin et al. *Am. J. Physiol.* 225, R744 (1988).

The actions of CRF in the peripheral and central nervous system are media ted through multiple binding sites. These CRF binding sites are heterogeneous with respect to sequence, pharmacology, and tissue distribution. Three CRF receptors, $CRF_1$, $CRF_{2\alpha}$ and $CRF_{2\beta}$, which encode 411-, 415-, and 431-amino acid proteins respectively, have been reported to date. The reported CRF receptors comprise seven putative membrane-spanning domains characteristic of $G_s$-coupled receptors. All three CRF receptors transduce a signal which involves stimulation of cAMP production.

A few classes of non-peptide CRF receptor antagonists have been reported in the past few years. Derivatives of 4-substituted thio-5-oxo-3-pyrazolines have been disclosed as CRF antagonists in U.S. Pat. No. 5,420,133. A weakly potent class of CRF antagonists has been reported in European patent application EP 0576350A1 (1993). Series of patent applications (WO 94/13643, WO 94/136344, WO 94/13661 and WO 94/13677) claiming non-peptide compounds as CRF antagonists have been reported by Pfizer and Co., Inc. The duPont Merck pharmaceutical company has recently disclosed a class of CRF antagonists, 1N-alkyl-N-arylpyrimidines and their derivatives in international patent application WO 95/10506.

SUMMARY OF THE INVENTION

According to the invention there are provided CRF ligands having structures defined by the general Formula I. The invention includes compounds used as intermediates in the preparation of the product compounds. Preferred intermediate compounds are those wherein the substituents K and L together include a carbonyl group. Preferred compounds are those whose synthesis is disclosed in Examples 3, 4, 7, 11, 12, 13, and 15–17.

According to another aspect of the invention there are provided methods for synthesis of the claimed compounds. According to yet another aspect of the invention there are provided pharmaceutical formulations comprising the compounds of the invention.

The invention also includes methods of treatment for diseases and disorders, including stress-related diseases, cardiovascular, neurological and psychiatric disorders including anxiety, depression, eating disorders, anorexia nervosa, superanuclear palsy, irritable bowel syndrome, gastrointestinal diseases, immune suppression, inflammatory disorders, drug and alcohol withdrawal symptoms, drug addiction, Alzheimer's disease or fertility disorders by administration of the compounds disclosed.

DETAILED DESCRIPTION OF THE PREFERRED EMBODIMENT

Substances which specifically inhibit the binding of CRF to its receptors are believed to block the physiological effects of CRF and these chemical entities would be useful in treating patients with CRF related disorders. The present invention discloses potent CRF receptor antagonists that are non-peptidic small molecules structurally distinct from those previously reported.

The compounds of the invention are of general formula I:

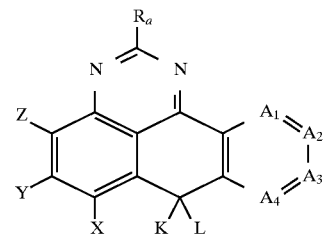

wherein $R_a$ is:

(a) H;
(b) $(C_1-C_6)$alkyl groups which are linear or branched, saturated or unsaturated and optionally substituted with amine, hydroxyl, halogen or carboxyl groups;
(c) allyl;
(d) $(C_3-C_6)$-cycloalkyl;
(e) aryl, wherein aryl is defined as phenyl or naphthyl unsubstituted or substituted with 1 or 2 or 3 substitutents selected from the group consisting of:
  (i) $(C_1-C_6)$ alkyl;
  (ii) $(C_3-C_7)$ alkenyl;
  (iii) $(C_3-C_7)$ cycloalkyl;
  (iv) $(C_1-C_6)$ alkoxy;
  (v) F; Cl; Br; I;
  (vi) $NO_2$;
  (vii) CN;
  (viii) $NH_2$:
  (ix) $NHCO(C_1-C_6)$ alkyl;
  (x) $NH(C_3-C_6)$ cycloalkyl;

(xi) $CO_2H$;
(xii) $CO_2(C_1-C_6)$alkyl;
(xiii) $CO_2(C_3-C_6)$cycloalkyl;
(xiv) $NHCONH(C_1-C_6)$alkyl;
(xv) $NHCO(C_3-C_6)$cycloalkyl;
(xvi) $NHSO_2-(C_1-C_6)$alkyl;
(xvii) $NHSO_2-(C_3-C_6)$cycloalkyl;
(xviii) $CONHSO_2-(C_1-C_6)$alkyl;
(xix) $CONHSO_2-(C_3-C_6)$cycloalkyl;
(xx) $CONHSO_2$-aryl;
(xxi) OH;
(xxii) $OCO-(C_1-C_6)$alkyl;
(xxiii) $OCO-(C_3-C_6)$cycloalkyl;
(xxiv) OCO-aryl;
(xxv) $CF_3$;
(xxvi) $(C_1-C_4)$alkylthio; or (f) heteroaryl, wherein heteroaryl is defined as an unsubstituted, monosubstituted or disubstituted heteroaromatic 5- or 6-membered cyclic moiety, which can contain one or two members selected from the group consisting of N, O, S and wherein the substitutents are selected from the group consisting of:
(i) Cl; Br; I; or F;
(ii) OH;
(iii) SH;
(iv) $NO_2$;
(v) $NH_2$;
(vi) $NH(C_1-C_6)$alkyl, or $NH(C_1-C_6)_2$alkyl;
(vii) $(C_1-C_5)$alkyl;
(viii) $(C_1-C_5)$alkoxy;
(ix) $(C_1-C_4)$-perfluoroalkyl; $CF_3$;
(x) $(C_2-C_4)$alkenyl;
(xi) $(C_2-C_4)$alkynyl;

Z is:
(a) H;
(b) $CO_2H$;
(c) $CO_2-(C_1-C_6)$alkyl;
(d) $CONH_2$;
(e) $CONH-(C_1-C_8)$;
(f) $CON-(C_1-C_8)_2$;
(g) $CONH-(C_1-C8)_2$;
(h) $CONH-(C_1-C8)-NH-(C_1-C_4)$alkyl;
(i) $CONH-(C_1-C_8)-NH-((C_1-C_4)$alkyl$)_2$;
(j) $CONH-(C_1-C_8)$cycloalkyl;
(k) $CONH-(C_1-C_8)$cycloalkyl-$NH_2$;
(l) $CONH-(C_1-C_8)$cycloalkyl-$NH-(C_1-C_4)$alkyl;
(m) $CONH-(Cl-C8)$cycloalkyl-$N-((C_1-C_4)$alkyl$)_2$;
(n) $CONH-(C_1-C_3)$alkyl-$(C_1-C_8)$cycloalkyl-$(C_1-C_3)$alkyl-$NH_2$;
(o) $CONH-(C_1-C_3)$alkyl-$(C_1-C_8)$cycloalkyl-$(C_1-C_3)$alkyl-$NH-(C_1-C_3)$alkyl;
(p) $NHCO-(C_1-C_8)-NH_2$;
(q) $NHCO-(C_1-C_8)$-cycloalkyl;
(r) $NHCO-(C_1-C_8)$-cycloalkyl-$NH_2$;
(s) $CONHNH(C_1-C_8)$alkyl-$NHNH_2$;
(t) $CONHNH(C_1-C_8)$cycloalkyl-$NHNH_2$;
(u) CN;
(v) $NO_2$;
(w) CHO;
(x) $SO_2NH-(C_1-C_8)-NH_2$;
(y) $SO_2NH-(C_1-C_8)$-cycloalkyl-$NH_2$;
(z) $NH-SO_2-(C_1-C_8)-NH_2$;
(aa) $NH-SO_2-(C_1-C_8)$cycloalkyl-$NH_2$;
(ab) imidazole and optionally C2-substituted derivatives thereof;
(ac) imidazoline and substituted derivatives thereof;
(ad) indole and substituted derivatives thereof;
(ae) piperazine and substituted derivatives thereof;
wherein the substitutents of groups (ab)–(ae) are selected from the group consisting of alkyl halides; carboxylic acids, amides and alkyl esters;

X and Y are independently:
(a) H;
(b) $NH(C_1-C_6)$-alkyl, straight or branched C—C chain;
(c) $N(C_1-C_6)_2$-alkyl, straight or branched C-C chain;
(d) $NH(C_1-C_6)$-alkyl-$NH_2$, straight or branched C—C chain;
(e) $N((C_1-C_6)$-alkyl-$NH_2)_2$, straight or branched C—C chain;
(f) CN;
(g) $(C_1-C_6)$-alkyl-$NH(C_1-C_6)$alkyl;
(h) $(C_1-C_6)$-alkyl-$O-(C_1-C_6)$;
(i) $NO_2$;
(j) -amidine;
(k) mono- and di-substituted amidines;
(l) guanidines;
(m) mono- and di-substituted guanidines;
(n) $(C_1-C_6)NH_2$;
(o) $NHCO-(C_1-C_6)$alkyl, NHCO-aryl, NHCO-heteroaryl;
(p) $NHCO-O(C_1-C_6)$alkyl, NHCO—O-aryl, NHCO—O-heteroaryl;
(q) $NHCONH(C_1-C_6)$alkyl, NHCONH-aryl, NHCONH-heteroaryl;
(r) $CONH(C_1-C_6)NH_2$;
(s) $CONH(C_3-C_6)$cycloalkyl-$NH_2$;
or alternatively, X and Y are joined to form one or two rings (ring size=5,6,7,8 membered cycloalkanes) through N or O or S;

X and Y are also independently:
(a) $NH-(CH_2)n-NH-$ (n=2,3,4,5,6,7,8);
(b) 1,2-diamino-cycloalkanes and substituted derivatives thereof;
(c) 1,2-diamino-cyclopropane and substituted derivatives thereof;
(d) 1,2-diamino-cyclobutane and substituted derivatives thereof;
(e) 1,2-diamino-cyclopentane and substituted derivatives thereof;
(f) 1,2-diamino-cyclohexane and substituted derivatives thereof;
(g) 1,2-diamino-cycloheptane and substituted derivatives thereof;
(h) 1,2-diamino-cyclooctane and substituted derivatives thereof;
(i) 1,2-phenylene diamine (1,2-diaminobenzene) and substituted derivatives thereof;
(j) 2,3-diaminopyridine;

K and L are independently:
(a) H;
(b) =O;
(c) OH;

(d) $(C_1-C_3)$ alkyl;
(e) $0-(C_1-C_3)$alkyl;
(f) $CH_2$;
(g) $CN$;
(h) $CO_2$-alkyl;
(i) $CO_2H$;
(j) $=N$-alkyl;
(k) $=N$-aryl;
(l) $=N$-heteroaryl;
(m) $=CHCO_2H$;
(n) $=CHCONH$-alkyl;
(o) $=CHCO_2$alkyl;

wherein the substituents of X, Y, K and L are selected from the substituent groups defined for R(b); R (e); R(f) and R(ab)–(ae).

A1, A2, A3, and A4 are independently:
(a) CH;
(b) $CH_2$;
(c) $CH=CH$;
(d) $CH_2—CH_2$;
(e) N;
(f) O;
(g) S;

or at least 2 of A1, A2, A3 and A4 combine to form a stable aryl, pyridyl, oxazole, isooxazole, thiophene, furan, pyrrole, thiazole, isothiazole or imidazole ring system by standard chemical methods or new methods devised for the purpose.

The invention also includes all enantiomers and stereoisomers of these compounds, and pharmaceutically acceptable salts thereof. A pharmaceutically acceptable salt is a physiologically non-toxic salt that does not interfere with the pharmacologic action of the CRF ligands of the invention. Suitable salts are disclosed in Berge. S. M. (1977) J. Pharmaceut. Sci. 66(1): 1–18.

Preferred compounds are benzoperimidine derivatives wherein X and Y of the general formula are incorporated into a diamino-cyclohexane ring system. Also preferred is a Z substituent comprising a carboxyl amide. Also preferred are benzoperimidine derivatives wherein A1-A2-A3-A4 forms a ring system that may be pyrrole, thiophene, furan, oxazole, isoxazole, thiazole, imidazole, or isothiazole. A ketone at K,L is a preferred structure for the chemical synthesis of these compounds.

The compounds disclosed herein are specifically designed as pharmacological agents, useful for, but not limited to, the treatment of the following conditions: stress-related diseases, cardiovascular, neurological and psychiatric disorders including anxiety, depression, eating disorders, anorexia nervosa, superanuclear palsy, irritable bowel syndrome, gastrointestinal diseases, immune suppression, inflammatory disorders, drug and alcohol withdrawal symptoms, drug addiction, Alzheimer's disease or fertility disorders.

The compounds according to the invention, which may also be referred to as active ingredients, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active ingredient.

The dosage for therapeutic use of the disclosed compounds can be determined using conventional considerations, including the clinical indication. It will be appreciated that the actual preferred amounts of active compound administered in a specific case will also vary according to specific active agent, the formulation, the route of administration. In general, a dose will be in the range of 0.1 to 120 mg per kilogram body weight of the recipient per day. The desired dose is preferably presented as two, three or more subdoses administered in unit dosage form.

For parenteral routes, such as intravenous, intrathecal, intramuscular and similar administration, typically doses are lower than the dose employed for oral administration.

The compounds may be administered alone or in combination with pharmaceutically acceptable carriers, in either single or multiple doses. Pharmaceutically acceptable carriers are defined as substances that are not toxic to the patient and that do not destroy the activity of the active compound. Pharmaceutical preparations containing the compounds of the invention in combination with various carriers are produced by conventional dissolving and lyophilizing processes to contain from approximately 0.1% to 100%, preferably from approximately 1% to 50% of the active ingredient. They can be prepared as ointments, salves, tablets, capsules, powders or sprays, together with effective excipients, vehicles, diluents, fragrances or flavor to make palatable or pleasing to use.

For parenteral administration, solutions of the novel compounds of formula I in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art. Suitable pharmaceutical carriers include inert solid diluents or fillers, sterile aqueous solution and various organic solvents. The pharmaceutical compositions formed by combining the compounds of formula I and the pharmaceutically acceptable carriers are then readily administered in a variety of dose forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient in the form of powder or granules, as a solution or suspension in an aqueous or nonaqueous liquid, or as an oil-in-water or water in oil liquid emulsion.

Tablets or other non-liquid oral compositions may contain acceptable excipients, known to the art for the manufacture of pharmaceutical compositions, comprising diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract.

Aqueous suspensions may contain the active ingredient in admixture with pharmacologically acceptable excipients, comprising suspending agents, such as methyl cellulose; and wetting agents, such as lecithin or long-chain fatty alcohols. The said aqueous suspensions may also contain preservatives, coloring agents, flavoring agents and sweetening agents in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms suitable for the disclosed routes of administration. The formulations may conveniently be presented in unit dosage form by methods known in the art of pharmacy.

The compounds of the invention are prepared as described below and are readily screened for receptor-binding using the binding assay of Example 32 and the biological assays of Examples 33–34.

The preparation of the compounds of the present invention is described in detail using the following examples, but the chemical reactions described are disclosed in terms of their general applicability to the preparation of the ligands of the invention. Occasionally, the reaction may not be applicable as described to each compound included within the disclosed scope of the invention. The compounds for which this occurs will be readily recognized by those skilled in the art. In all such cases, either the reactions can be successfully performed by conventional modifications known to those skilled in the art, that is, by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials; all temperatures are set forth in degrees Celsius; and, unless otherwise indicated, all parts and percentages are by weight.

SYNTHESIS

The preparation of the compounds of the present invention is described in detail using the following examples, but the chemical reactions described are disclosed in terms of their general applicability to the preparation of the ligands of the invention. Occasionally, the reaction may not be applicable as described to each compound included within the disclosed scope of the invention. The compounds for which this occurs will be readily recognized by those skilled in the art. In all such cases, either the reactions can be successfully performed by conventional modifications known to those skilled in the art, that is, by appropriate protection of interfering groups, by changing to alternative conventional reagents, or by routine modification of reaction conditions. Alternatively, other reactions disclosed herein or otherwise conventional will be applicable to the preparation of the corresponding compounds of the invention. In all preparative methods, all starting materials are known or readily preparable from known starting materials; all temperatures are set forth in degrees Celsius; and, unless otherwise indicated, all parts and percentages are by weight.

The benzoperimidine derivatives of the general structure I were prepared by the general schemes 1 to 5 shown below. A representative example of the general structure I, where R=H; Z=CO$_2$H; X and Y=H; K and L=(=O) and A1, A2, A3, A4 each are C, was used as a starting material to synthesize the derivative products. Similar reaction sequence(s) may be applied towards the synthesis of other derivatives.

SCHEME 1

Method A involves conversion of the carboxylic group to amide in step 1 using 1, 1'-carbonyldiimidazole (CDI) as a coupling agent in DMF as a solvent at room temperature. The resulting amide was further treated in step 2 with a different amine or diamine to give the product as shown below.

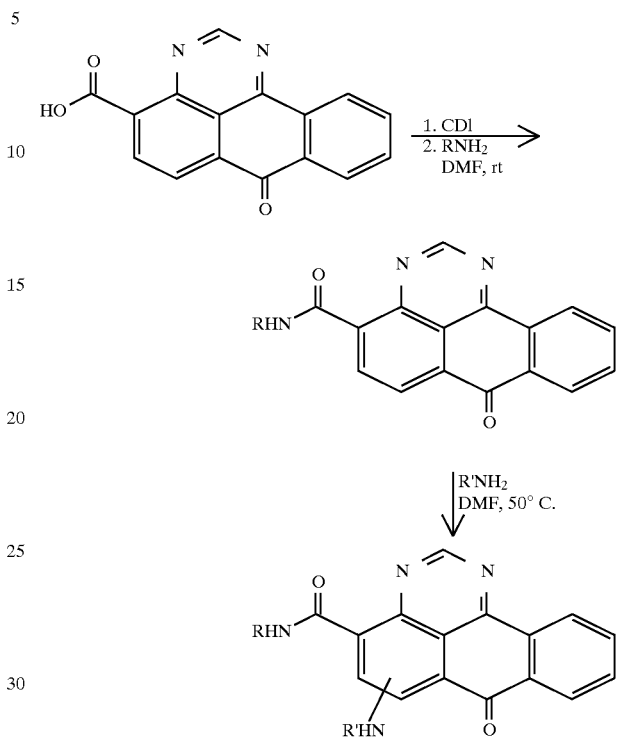

SCHEME 2

In Method B, 7-oxo-benzo[e]perimidine-4-carboxylic acid was treated with 1, 1'-carbonyldiimidazole in DMF at 100° C. Four different products, besides the expected imidazole amide were isolated as shown below.

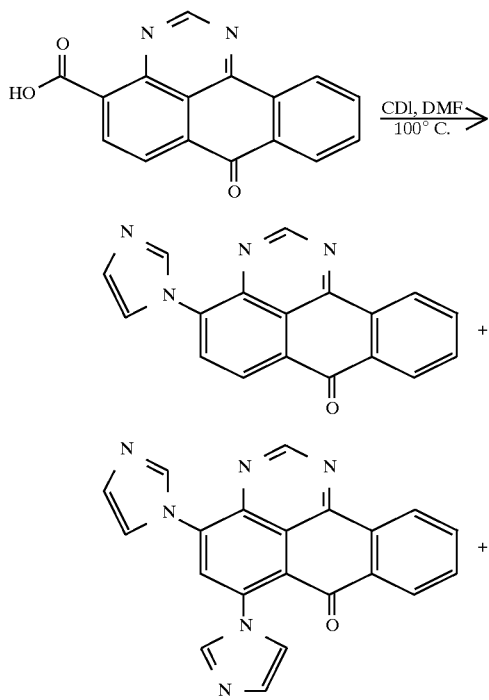

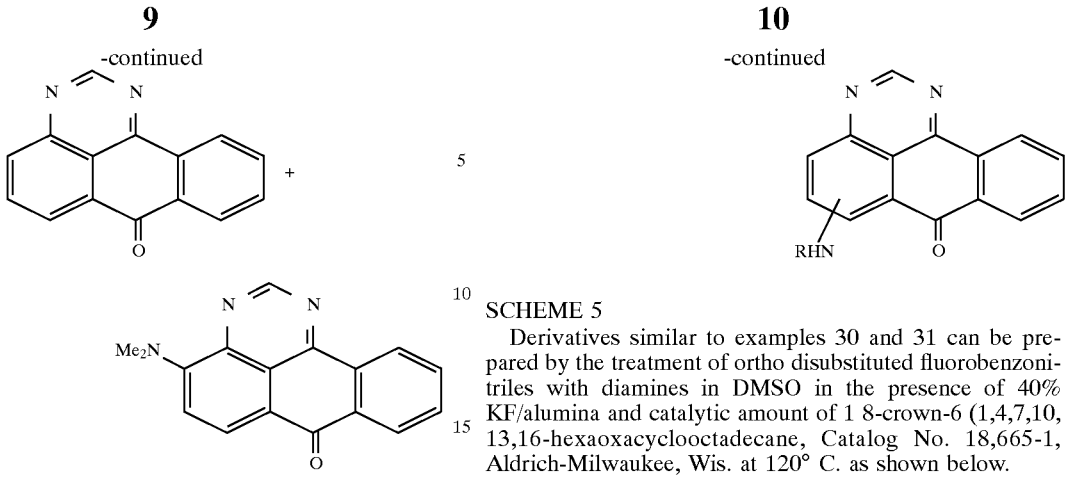

SCHEME 3

Method C involves the synthesis of derivatives of 7-oxo-benzo[e]perimidine-4-carboxylic acid by using one particular amine or diamine or a mixture of two different amines or diamines in the presence of 1,1'-carbonyldiimidazole as shown below.

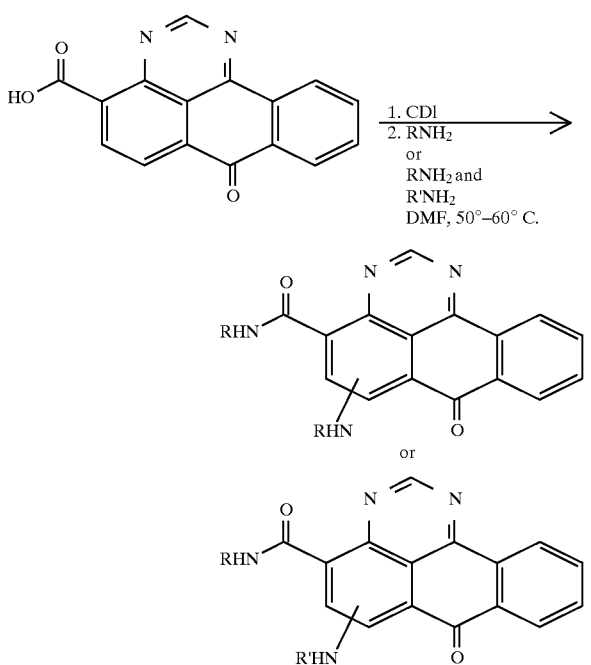

SCHEME 4

In method D, 7-oxo-benzo[e]perimidine-4-carboxylic acid was treated with an amine in the absence of 1,1'-carbonyldiimidazole for 48 h at 60° C. A decarboxylated product was isolated as shown below.

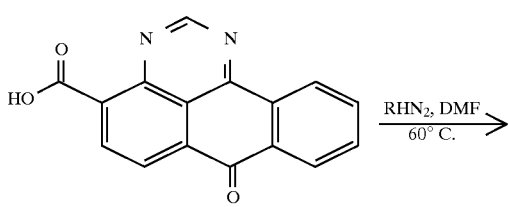

SCHEME 5

Derivatives similar to examples 30 and 31 can be prepared by the treatment of ortho disubstituted fluorobenzonitriles with diamines in DMSO in the presence of 40% KF/alumina and catalytic amount of 1 8-crown-6 (1,4,7,10,13,16-hexaoxacyclooctadecane, Catalog No. 18,665-1, Aldrich-Milwaukee, Wis. at 120° C. as shown below.

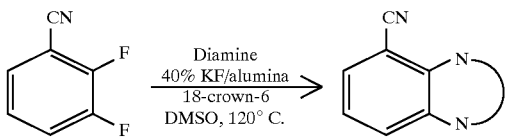

General Methods for Preparation of Compounds of General Formula I

Method A

Step 1

To a solution of 0.276 g (1 mmol) of 7-oxo-7H-benzo[e] perimidine-4-carboxylic acid in 15 mL of dry DMF at 20° C. was added 0.162 g (1 mmol) of 1,1'-carbonyldiimidazole and the reaction mixture was stirred for 60 min. Next a solution of 1 mmol of the corresponding amine or diamine in 3 mL of dry DMF was added. The reaction was stirred for 18 h and final product was chromatographed on Waters Prep L.C. 4000 System: column PrePakR cartridge VydacTM $C_18$ (47×300 mm); UV absorbance, 2.0 AUFS @ 230; buffer A 0.1% TFA; buffer B, 0.1% TFA in 60% $CH_3CN$/40% $H_2O$; flow rate, 95 mL/min; gradient 20% B to 90% B in 40 minutes.

Step 2

To a solution of 0.1 mmol of 7-oxo-7H-benzo[e] perimidine-4-carboxamide derivative (step A) in 10 mL of dry DMF was added a solution of 1 mmol of the corresponding diamine in 2 mL of dry DMF. The reaction was stirred for 6 h at 50° C. and product was chromatographed on Waters Prep L.C. 4000 System: PrePak® cartridge Vydac™ $C_18$ (47×300 mm); UV absorbance, 2.0 AUFS @ 230; buffer A, 0.1% TFA; buffer B, 0.1% TFA in 60% $CH_3CN$/40% $H_2O$; flow rate, 95 mL/min; gradient 20% B to 100% B in 40 min.

Method B

To a solution of 0.276 g (1 mmol) of 7-oxo-7H-benzo[e] perimidine-4-carboxylic acid in 20 mL of dry DMF was added 0.162 g (1mmol) of 1,1'-carbonyldiimidazole and the reaction mixture was stirred for 18 h at 100° C. Product was chromatographed on Waters Prep L.C. 4000 System: column, PrePak® cartridge Vydac™ $C_18$ (47×300 mm); UV absorbance, 2.0 AUFS @ 230; buffer A, 0.1% TFA; buffer B, 0.1% TFA in 60% $CH_3CN$/40% $H_2O$; flow rate, 95 mL/min; gradient 20% B to 85% B in 60 min.

Method C

To a solution of 0.276 g (1 mmol) of 7-oxo-7H-benzo[e] perimidine-4-carboxylic acid in 15 mL of dry DMF at 20° C.

was added for 0.62 g (1mmol) of 1,1'carbonyldiimidazole and the reaction mixture was stirred for 60 min. Next a solution of 1 mmol of the corresponding amine or diamine in 3 mL of dry DMF was added. The reaction was stirred for 18 h at 50°–60° C. and chromatographed on Waters Prep L.C. 4000 System: column, PrePak® cartridge Vydac™ $C_{18}$ (47×300 mm); UV absorbance, 2.0 AUFS @ 230; buffer A, 0.1% TFA; buffer B, 0.1% TFA in 60% $CH_3CN$/40% $H_2O$; flow rate, 95 mL/min; gradient 20% B to 90% B in 40 min.

Method D

To a solution of 1 mmol of 7-oxo-7H-benzo[e]perimidine-4-carboxamide in 10 mL of dry DMF was added a solution of 1 mmol of the corresponding amine or diamine in 5 mL of dry DMF. The reaction was stirred for 48 h at 60° C. and product was chromatographed on Waters Prep L.C. 4000 System: column, PrePak® cartridge Vydac™ C18 (47×300 mm); UV absorbance, 2.0 AUFS @ 230; buffer A, 0.1% TFA; buffer B, 0.1% TFA in 60% $CH_3CN$/40% $H_2O$; flow rate, 95 mL/min.; gradient 10% B to 90% B in 40 min.

EXAMPLE 1

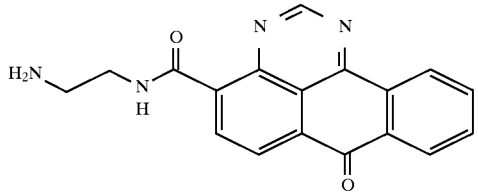

Preparation 0.276 g (1 mmol) of 7-oxo-7H-benzo[e]perimidine-4-carboxylic acid was treated with 0.162 g (1 mmol) of 1,1'-carbonyldiimidazole and 0.062 g (1 mmol) of ethylenediamine and the reaction mixture was chromatographed (method A, step 1) to afford 0.222 g (70%) of the title compound: mp 208°–210° C.; $^1$H NMR (300 MHz, DMSO-$d_6$) δ6 10.28–10.32 (m, 1H), 9.59 (s, 1H), 8.75–8.78 (m, 2H), 8.53–8.58 (m, 1H), 8.25–8.30 (m, 1H), 7.86–8.00 (m, 5H), 3.69–3.74 (m, 2H), 3.09–3.14 (m, 2H); APCIMS m/z 319 (M+1).

EXAMPLE 2

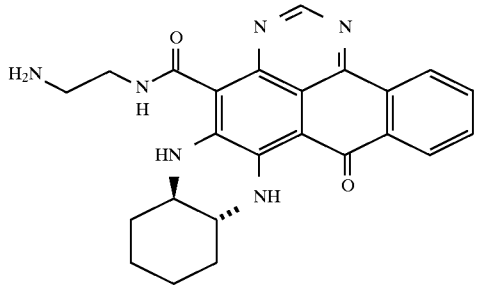

Preparation
The product of example 1 (0.031 g, 0.1 mmol) was treated with 0.114 g (1 mmol) of (1R,2R)-(−)-1,2-diaminocyclohexane and the reaction mixture was chromatographed (method A, step 2) to afford 0.033 g (80%) of the title compound: mp 128°–132° C.; $^1$H NMR (300 MHz, DMSO-$d_6$) δ11.94 (s, 1H), 11.75 (s, 1H), 11.20 (s, 1H), 8.99 (s, 1H), 8.76–8.83 (m, 1H), 8.67–8.75 (m, 1H), 8.30 (d, J=7.64, 1H), 8.23 (d, J=7.58, 1H), 7.75–7.97 (m, 7H), 3.57–3.67 (m, 2H), 3.48–3.56 (m, 1H) 3.13–3.23 (m, 1H), 3.02–3.12 (m, 2H) 2.10–2.23 (m, 1H), 2.00–2.10 (m, 1H)1.77–1.188 (m, 2H) 1.35–1.52 (m, 4H); APCIMS m/z 429 (M+1).

EXAMPLE 3

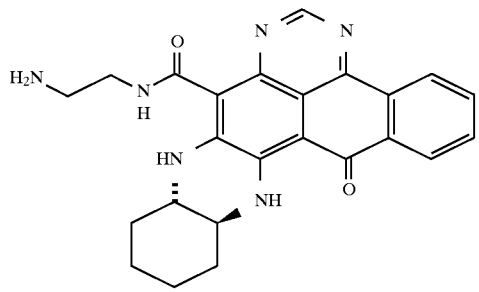

Preparation

The product of example 1 (0.031 g, 0.1 mmol) was treated with 0.114 g (1 mmol) of (1S,2S)-(+)-1,2-diaminocyclohexane and the reaction mixture was chromatographed (method A, step 2) to afford 0.032 g (78%) of the title compound: mp 228°–230° C.; $^1$H NMR (300 MHz, DMSO-$d_6$) δ8 12.01 (s, 1H), 11.78 (brs, 1H), 11.23 (s, 1H), 9.05 (s, 1H), 8.84 (d, J=7.62, 1H), 8.35 (d, J=7.57, 1H), 7.78–7.95 (m, 5H), 6.56 (brs. 1H) 3.55–3.74 (m, 2H), 3.00–3.25 (m, 4H), 2.13–2.25 (m, 1H), 2.03–2.12 (m, 1H), 1.75–1.90 (m, 2H), 1.35–1.55 (m, 4H); APCIMS m/z 429 (M+1).

EXAMPLE 4

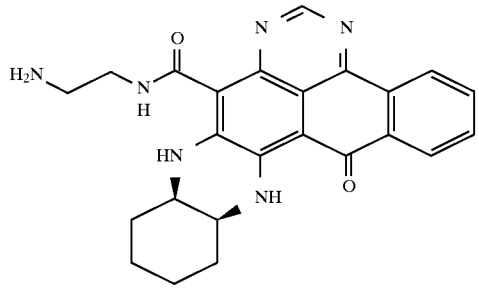

Preparation

The product of example 1 (0.031 g, 0.1 mmol) was treated with 0.114 g (1 mmol) of cis-1,2-diaminocyclohexane and the reaction mixture was chromatographed (method A, step 2) to afford 0.039 g (90%) of the title compound: mp 138°–140° C.; APCIMS m/z 429 (M+1).

EXAMPLE 5

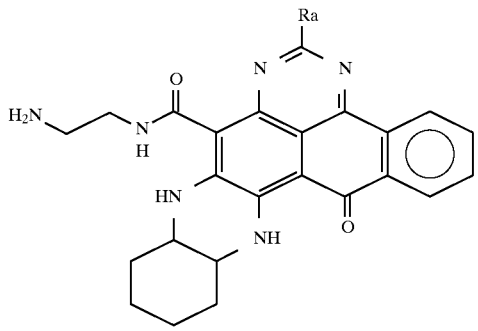

Preparation 0.276 g (1 mmol) of 7-oxo-7H-benzo[e]perimidine-4-carboxylic acid was treated with 0.162 g (1 mmol) of 1,1'-carbonyldiimidazole, 0.062 g (1 mmol) of ethylenediamine and 0.114 g (1 mmol) of cis-1,2-diaminocyclohexane, the reaction mixture was chromatographed (method C) to afford 0.010 g (2.9%) of the title compound: mp 132°–134° C.; APCIMS m/z 347 (M+1).

EXAMPLE 6

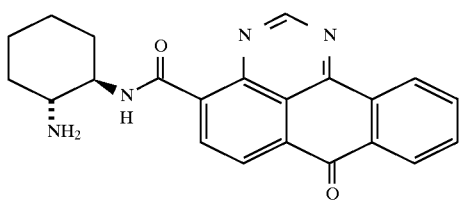

Preparation 0.276 g (1 mmol) of 7-oxo-7H-benzo[e]perimidine-4-carboxylic acid was treated with 0.162 g (1 mmol) of 1,1'-carbonyldiimidazole and 0.114 g (1 mmol) of (1R,2R)-(−)-1,2-diaminocyclohexane and the reaction mixture was chromatographed (method A, step 1) to afford 0.268 g (72%) of the title compound: mp 167°–170° C.; $^1$H NMR (300 MHz, DMSO-$d_6$) δ8 10.19 (d, J=8.73, 1H), 9.56 (s, 1H), 8.71–8.77 (m, 2H), 8.53 (d, J=7.66, 1H), 8.23 (d, J=7.65, 1H), 8.16 (brs, 2H), 7.91–7.98 (m, 1H), 7.83–7.89 (m, 1H), 4.05–4.16 (m, 1H) 3.18–3.31 (m, 1H), 2.04–2.17 (m, 2H), 1.75–1.90 (m, 2H), 1.45–1.70 (m, 2H), 1.32–1.45 (m, 2H); APCIMS m/z 373 (M+1).

EXAMPLE 7

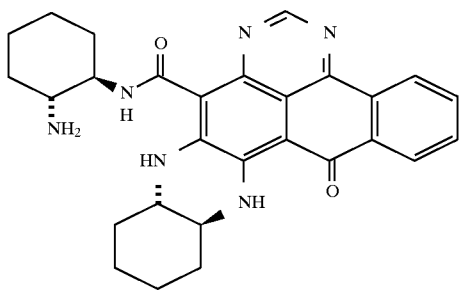

Preparation

The product of example 6 (0.037, 0.1 mmol) was treated with 0.114 g (1 mmol) of (1S,2S)-(+)-1,2-diaminocyclohexane and the reaction mixture was chromatographed (method A, step 2) to afford 0.038 g (80%) of the title compound: mp 165°–167° C.; $1^1$H NMR (300 MHz, DMSO-$d_6$) d 12.06 (s, 1H), 11.67 (d, J=8.42,1 1H) 10.89 (s, 1H) 9.13 (s, 1H), 8.90 (d, J=7.24, 1H), 8.41 (d, J=6.91, 1H), 7.97 (brs, 2H), 7.90–7.96 (m, 1H), 7.83–7.88 (m, 1H), 3.97–4.10 (m, 1H), 3.32–3.43 (m, 1H), 3.11–3.27 (m, 2H), 2.17–2.27 (m, 1H), 1.98–2.10 (m, 3H), 1.73–1.90 (m, 4H), 1.30–1.70 (m, 8H); APCIMS m/z 483 (M+1).

EXAMPLE 8

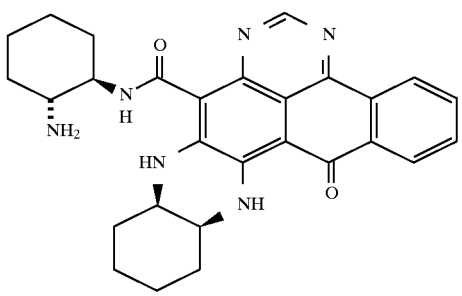

Preparation

The product of example 6 (0.037, 0.1 mmol) was treated with 0.114 g (1 mmol) of cis-1,2-diaminocyclohexane and the reaction mixture was chromatographed (method A, step 2) to afford 0.043 g (89%) of the title compound: mp 184°–186° C.; APCIMS m/z 483 (M+1).

EXAMPLE 9

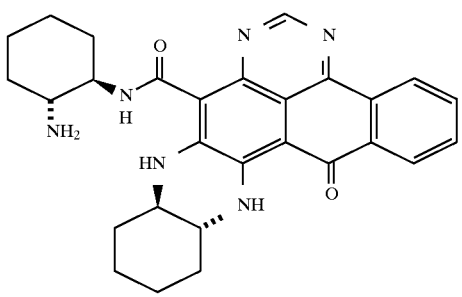

Preparation

The product of example 6 (0.037, 0.1 mmol) was treated with 0.114 g (1 mmol) of (1R,2R)-(−)-1,2-diaminocyclohexane and the reaction mixture was chromatographed (method A, step 2) to afford 0.043 g (90%) of the title compound: mp 208°–212° C.; APCIMS m/z 483 (M+1).

EXAMPLE 10

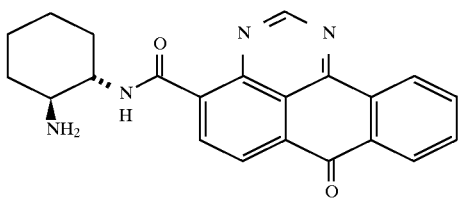

Preparation 0.276 g (1 mmol) of 7-oxo-7H-benzo[e]perimidine-4-carboxylic acid was treated with 0.162 g (1 mmol) of 1,1'-carbonyldiimidazole and 0.114 g (1 mmol) of (1S,2S)-(+)-1,2-diaminocyclohexane and the reaction mixture was chromatographed (method A, step 1) to afford 0.223 g (60%) of the title compound: ¹H NMR (300 MHz, DMSO-d₆) d 10.21 (d, J=8.82, 1H), 9.66 (s, 1H), 8.88 (d, J=7.72, 1H), 8.82 (d, J=7.65, 1H), 8.65 (d, J=7.64, 1H), 8.36 (d, J=7.64, 1H), 7.99–8.07 (m, 2H), 7.90–7.97 (m, 1H), 4.03–4.17 (m, 1H), 3.10–3.25 (m, 1H), 1.95–2.10 (m, 2H), 1.70–1.85 (m, 2H), 1.40–1.70 (m, 2H), 1.30–1.40 (m, 2H); APCIMS m/z 373 (M+1)

EXAMPLE 11

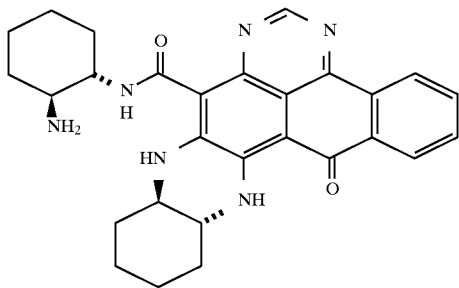

Preparation

The product of example 10 (0.037, 0.1 mmol) was treated with 0.114 g (1 mmol) of (1R,2R)-(−)-1,2-diaminocyclohexane and the reaction mixture was chromatographed (method A, step 2) to afford 0.038 g (78%) of the title compound: mp 190°–193° C.; ¹H NMR (300 MHz, DMSO-d₆) d 12.05 (s, 1H),11.66 (d, J=8.37, 1H) 10.88 (s, 1H) 9.12 (s, 1H), 8.89 (d, J=7.76, 1H), 8.40 (d, J=7.75, 1H), 7.98 (brs, 2H), 7.90–7.95, (m, 1H), 7.82–7.87 (m, 1H), 4.00–4.09 (m, 1H), 3.34–3.42 (m, 1H), 3.10–3.26 (m, 2H), 2.18–2.27 (m, 1H), 1.98–2.10 (m, 3H), 1.73–1.90 (m, 4H), 1.30–1.70 (m, 8H); APCIMS m/z 483 (M+1).

EXAMPLE 12

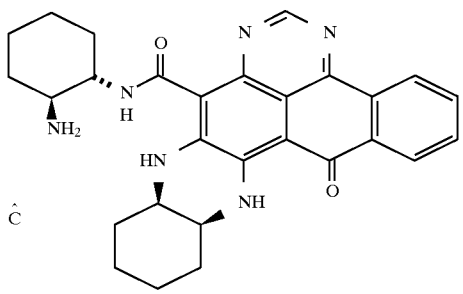

Preparation

The product of example 10 (0.037, 0.1 mmol) was treated with 0.114 g (1 mmol) of cis-1,2-diaminocyclohexane and the reaction mixture was chromatographed (method A, step 2) to afford 0.035 g (73%) of the title compound: mp 185°–187° C.; ¹H NMR (300 MHz, DMSO-d₆) d 12.29 (s, 1H), 11.72 (s, 1H), 11.01 (s, 1H), 9.13 (s, 1H), 8.93 (d, J=7.49, 1H), 8.45 (d, J=7.61, 1H), 8.00 (brs, 3H), 7.82–7.97 (m, 2H), 3.80–4.40 (m, 3H), 3.10–3.40 (m, 1H), 1.20–2.20 (m, 16H); APCIMS m/z 483 (M+1).

EXAMPLE 13

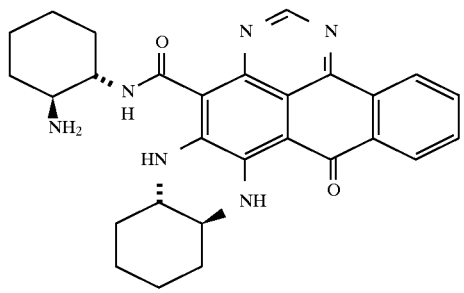

Preparation

The product of example 10 (0.037, 0.1 mmol) was treated with 0.114 g (1 mmol) of (1S,2S)-(+)-1,2-diaminocyclohexane and the reaction mixture was chromatographed (method A, step 2) to afford 0.037 g (77%) of the title compound: mp >250° C.; APCIMS m/z 483 (M+1).

EXAMPLE 14

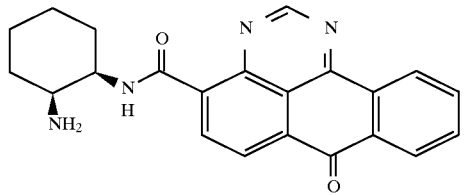

Preparation 0.276 g (1 mmol) of 7-oxo-7H-benzo[e]perimidine-4-carboxylic acid was treated with 0.162 g (1 mmol) of 1,1'-carbonyldiimidazole and 0.114 g (1 mmol) of cis-1,2-diaminocyclohexane and the reaction mixture was chromatographed (method A, step 1) to afford 0.300 g (80.6%) of the title compound: mp 172°–175° C.; ¹H NMR (300 MHz, DMSO-d₆) d 10.89 (d, J=8.82, 1H), 9.71 (s, 1H), 8.90 (d, J=7.71, 1H), 8.85 (d, J=7.30, 1H), 8.63 (d, J=7.67, 1H), 8.33 (d, J=7.28, 1H), 7.88–8.05 (m, 5H), 4.62–4.67 (m, 1H), 3.35–3.53 (m,1H), 1.75–1.95 (m, 4H), 1.55–1.75 (m, 3H), 1.35–1.55 (m, 1H); APCIMS m/z 373 (M+1).

EXAMPLE 15

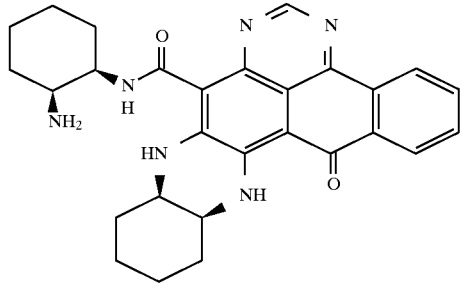

Preparation

The product of example 14 (0.037g, 0.1 mmol) was treated with 0.114 g (1 mmol) of cis-1,2-diaminocyclohexane and the reaction mixture was chromatographed (method A, step 2) to afford 0.024 g (50%) of the title compound: mp 146°–150° C.; APCIMS m/z 483 (M+1).

EXAMPLE 16

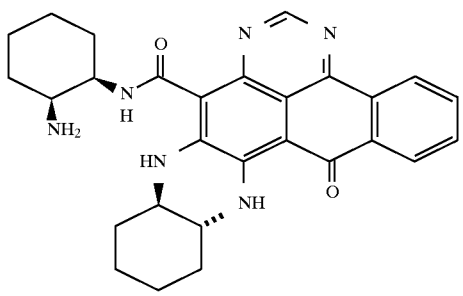

Preparation

The product of example 14 (0.037g, 0.1 mmol) was treated with 0.114 g (1 mmol) of (1 R,2R)-(−)-1,2-diaminocyclohexane and the reaction mixture was chromatographed (method A, step 2) to afford 0.034 g (66%) of the title compound: mp 238°–242° C.; APCIMS m/z 483 (M+1).

EXAMPLE 17

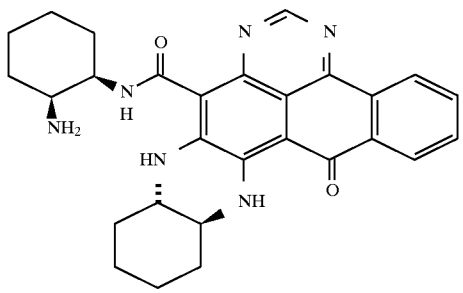

Preparation

The product of example 14 (0.037g, 0.1 mmol) was treated with 0.114 g (1 mmol) of (1S,2S)-(+)-1,2-diaminocyclohexane and the reaction mixture was chromatographed (method A, step 2) to afford 0.036 g (75%) of the title compound: mp 180°–183° C.; APCIMS m/z 483 (M+1).

EXAMPLE 18

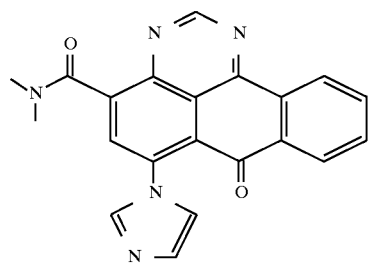

Preparation 0.276 (1 mmol) of 7-oxo-7H-benzo[e]perimidine-4-carboxylic acid was treated with 0.162 g (1 mmol) of 1,1'-carbonyldiimidazole in DMF and the reaction mixture was chromatographed (method B) to afford 0.012 g (3.2%) of the title compound: mp 173°–175° C.; APCIMS m/z 370 (M+1).

EXAMPLE 19

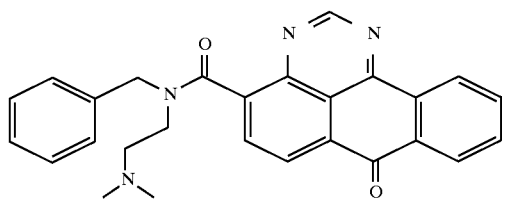

Preparation 0.276 g (1 mmol) of 7-oxo-7H-benzo[e]perimidine-4-carboxylic acid was treated with 0.162 g (1 mmol) of 1,1'-carbonyldiimidazole and 0.178 g of N'-benzyl-N,N-dimethylethylenediamine, and the reaction mixture was chromatographed (method A, step 1) to afford 0.283 g (65%) of the title compound: mp 74°–76° C.; APCIMS m/z 437 (M+1).

EXAMPLE 20

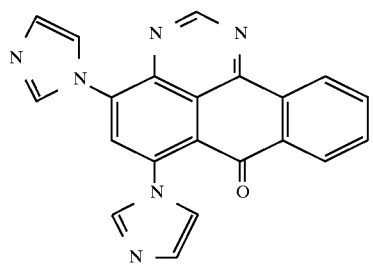

Preparation 0.276 (1 mmol) of 7-oxo-7H-benzo[e]perimidine-4-carboxylic acid was treated with 0. 162 g (1 mmol) of 1,1'-carbonyldiimidazole and the reaction mixture was chromatographed (method B) to afford 0.020 g (5.5%) of the title compound: mp 128°–132° C.; APCIMS m/z 365 (M+1).

EXAMPLE 21

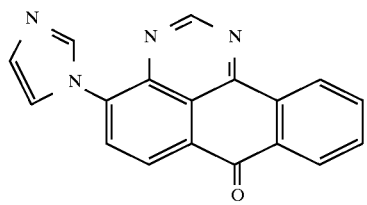

Preparation 0.276 g (1 mmol) of 7-oxo-7H-benzo[e]perimidine-4-carboxylic acid was treated with 0.162 g (1 mmol) of 1,1'-carbonyldiimidazole and the reaction mixture was chromatographed (method B) to afford 0.050 g (16.8%) of the title compound: mp 142°–144° C.; $^1$H NMR (300 MHz, DMSO-$d_6$) d 9.62 (d, J=1.98, 1H), 9.16 (s, 1H), 8.85 (d, J=7.76, 1H), 8.61–8.67 (m, 1H), 8.46–8.51 (m, 1H), 8.34 (d, J=7.68 1H), 7.96–8.04 (m, 1H), 7.88–7.95 (m, 1H), 7.63 (s, 1H); APCIMS m/z 299 (M+1).

EXAMPLE 22

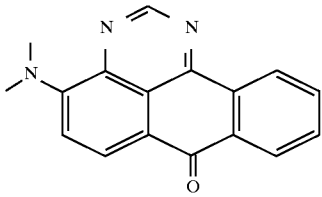

Preparation 0.276 g (1 mmol) of 7-oxo-7H-benzo[e]perimidine-4-carboxylic acid was treated with 0.162 g (1 mmol) of 1,1'-carbonyldiimidazole in DMF and the reaction mixture was chromatographed (method B) to afford 0.008 g (2.6%) of the title compound:mp >250° C.; $^1$H NMR (300 MHz, DMSO-$d_6$) d 9.58 (s, 1H), 8.65 (dd, J=7.76, 1.06, 1H), 8.55 (d, J=7.44, 11H), 8.34 (dd, J=7.68, 1.10, 1H), 8.15 (d, J=7.43, 1H), 7.96–8.03 (m, 1H), 7.86–7.95 (m, 1H), 3.15 (s, 3H), 2.76 (s, 3H); APCIMS m/z 304 (M+1).

EXAMPLE 23

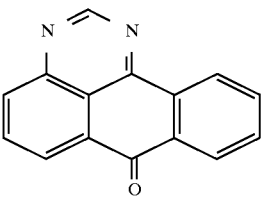

Preparation 0.276 g (1 mmol) of 7-oxo-7H-benzo[e]perimidine-4-carboxylic acid was treated with 0.162 g (1 mmol) of 1,1'-carbonyldiimidazole and the reaction mixture was chromatographed (method B) to afford 0.080 g (34%) of the title compound: mp >250° C.; APCIMS m/z 233 (M+1).

EXAMPLE 24

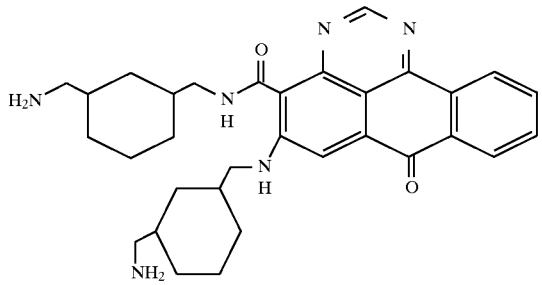

Preparation 0.276 g (1 mmol) of 7-oxo-7H-benzo[e]perimidine-4-carboxylic acid was treated with 0.162 g (1 mmol) of 1,1'-carbonyldiimidazole and 0.142 g (1 mmol) of 1,3-cyclohexanebis (methylamine), and the reaction mixture was chromatographed (method C) to afford 0.062 g (11%) of the title compound: mp 192°–194° C.; APCIMS m/z 541 (M+1).

EXAMPLE 25

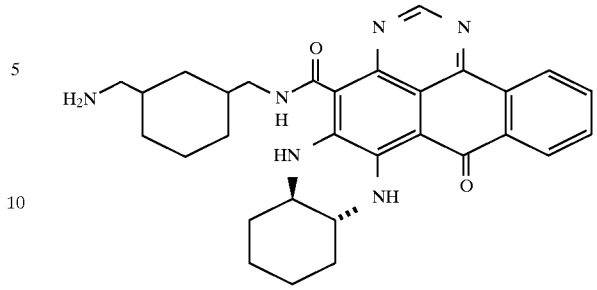

Preparation 0.276 g (1 mmol) of 7-oxo-7H-benzo[e]perimidine-4-carboxylic acid was treated with 0.162 g (1 mmol) of 1,1'-carbonyldiimidazole, 0.142 g (1 mmol) of 1,3-cyclohexanebis (methylamine), and 0.114 g (1 mmol) of (1S,2S)-(+)-1,2-diaminocyclohexane, and the reaction mixture was chromatographed (method C) to afford 0.015 g (2.9%) of the title compound: mp 193°–195° C.; APCIMS m/z 511 (M+1).

EXAMPLE 26

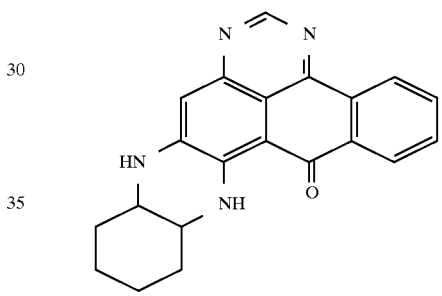

Preparation 0.276 g (1 mmol) of 7-oxo-7H-benzo[e]perimidine-4-carboxylic acid was treated with 0.114 g (1 mmol) of trans-1,2-diaminocyclohexane, and the reaction mixture was chromatographed (method D) to afford 0.020 g (5.8%) of the title compound: mp 198°–200° C.; APCIMS m/z 343 (M+1).

EXAMPLE 27

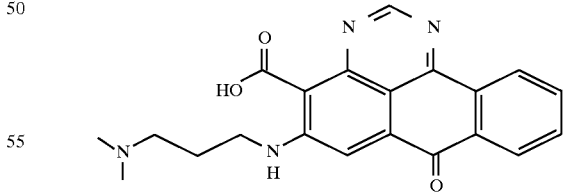

Preparation 0.276 g (1 mmol) of 7-oxo-7H-benzo[e]perimidine-4-carboxylic acid was treated with 0.162 g (1 mmol) of 1,1'-carbonyldiimidazole, and 0.187 g (1 mmol) of 3,3'-iminobis(N,N-dimethylpropylamine), and the reaction mixture was chromatographed (method C) to afford 0.015 g (4%) of the title compound: mp 188°–190° C.; APCIMS m/z 376 (M+1).

EXAMPLE 28

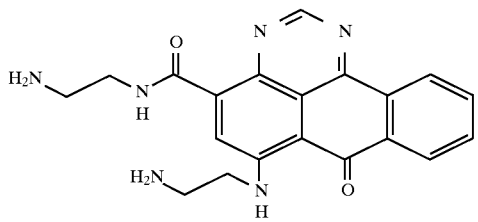

Preparation

The product of Example 1 (0.031, 0.1 mmol) was treated with 0.62 g (1 mmol) of ethylene diamine and the reaction was chromatographed (method A, step 2) to afford 0.11 g (29%) of the title compound: mp >250° C.; NMR (300 MHz, MeOH-$d_4$) d 9.00–9.15 (s, 1H), 8.55–8.90 (d, 1H), 8.10–8.40 (m, 2H), 7.55–7.9 (m, 2H), 3.55–4.00 (m, 4H), 3.25–3.45 (m, 4H); APCIMS m/z 379 (M+1).

EXAMPLE 29

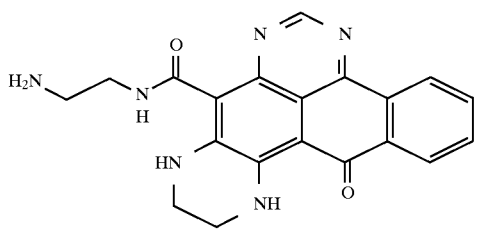

Preparation

The product of Example 1 (0.031, 0.1 mmol) was treated with 0.60 g (1 mmol) of ethylene diamine and the reaction was chromatographed (method A, step 2) to afford 0.10 g (26%) of the title compound; mp 155°–157° C.; $^1$H NMR (300 MHz, MeOH-$d_4$) d 9.00–9.15 (s, 1H), 8.35–8.45 (d, 1H), 8.20–8.35 (d, 1H), 7.75–7.90 (m, 2H), 3.95–4.05 (m, 2H), 3.25–3.65 (m, 6H); APCIMS m/z 374 (M+1).

EXAMPLE 30

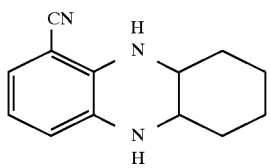

Preparation

To a mixture of 1 mL each of 0.1M solution of 2,3-difluorobenzonitrile and 1,2 diaminocyclohexane in DMSO was added 100 mg of KF/alumina and 10 mg of 18-crown-6, and the reaction mixture stirred at 120° C. for 14 h. After workup the crude was loaded on a silica gel column and the products isolated by flash chromatography: mp 120°–122° C.; $^1$H NMR(300 MHz, CDCl$_3$): 6.70–6.75(dd, 1H, Ar), 6.45–6.55(dd, 1H, Ar), 6.40–6.45(t, 1H, Ar), 4.15–4.35(s-br, 1H, NH), 3.50–3.95(s-br, 1H, NH), 2.95–3.05(m, 1H), 2.60–2.95(m, 1H), 1.55–2.00(m, 4H), 1.05–1.45(m, 4H); APCIMS m/z 214 (M+1).

EXAMPLE 31

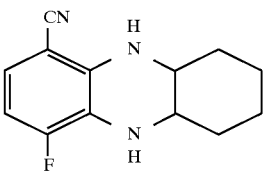

Preparation

To a mixture of 1 mL each of 0.1M solution of 2, 3, 4-trifluorobenzonitrile and 1,2 diaminocyclohexane in DMSO was added 100 mg of KF/alumina and 10 mg of 18-crown-6, and the reaction mixture stirred at 120° C. for 14 h. After workup the crude was loaded on a silica gel column and the products isolated by flash chromatography: mp 163°–167° C.; $^1$H NMR(300 MHz, CDCl$_3$): 6.50–6.65 (d, 1H, Ar), 5.90–6.10(d, 1H, Ar), 3.85–4.05(s-br, 1H, NH), 3.55–3.65(s-br, 1H, NH), 2.7–2.85(m, 1H), 2.55–2.65(m, 1H), 1.40–1.85(m, 4H), 0.95–1.25(m, 4H); APCIMS m/z 232 (M+1).

BIOLOGICAL EVALUATION

EXAMPLE 32

Isolation of CRF Membrane Receptors

Cell Culture

Human embryonic kidney 293-EBNA cells stably transfected with cDNA for rat CRF$_1$ (Chang et al., 1993) or mouse CRF$_{2b}$ (Kishimoto et al., 1995) receptors were generously provided by Dr. M. G. Rosenfeld, Howard Hughes Medical Institute, University of California at San Diego. Cells were cultured in Dulbecco's modified Eagle's medium supplemented with 5% fetal bovine serum, 5% neonatal calf serum, 100 U/ml Penicillin-G/Streptomycin, 2 μg/ml Fungizone™ and 10 U/ml Hygromycin-B.

Membrane Preparation

Fresh or frozen 293-EBNA cells were homogenized in approximately 50 ml of homogenization buffer (buffer A) containing 50 mM Tris, 2 mM EGTA and 0.32M Sucrose (pH 7.4) using an Ultra-Turax homogenizer (Tekmar Company, Cincinnati, Ohio) at 80% maximal setting three times for 10 sec. Cell pellets were centrifuged at 4° C. at 1000×g for 10 min in a Beckman GS-6R centrifuge. Pellets were resuspended in buffer A, homogenized and centrifuged as described above. Pooled supernatants were transferred to centrifuge bottles (Beckman) and centrifuged at 4° C. at 20,000×g for 30 min in a Beckman J2-HS centrifuge. Cell pellets were resuspended in buffer A and again were centrifuged at 4° C. at 20,000×g for 30 min. Cell pellets were resuspended in buffer A and stored at −70° C. in aliquots of 2.5-5 mg/ml total membrane protein. Total membrane protein was determined by a BCA kit (Pierce, Rockford, Ill.).

Radioligand Binding Assays

Membranes were thawed and resuspended in binding assay buffer containing: 50 mM HEPES (pH 7.4), 2 mM EGTA, 0.1% BSA, 5 mM MgCl$_2$ and 0.01% bacitracin. Membranes (15–25 μg protein/tube) were incubated in duplicate with $^{125}$I-Tyr$^0$-oCRF (25,000 CPM/tube; 2200 Ci/mmol) and various compounds for 1 hr at room temp. Compounds were dissolved in 100% DMSO and were tested in binding assay buffer containing final concentrations of 1 pM-100 μM in 10% DMSO final. Nonspecific binding was determined in the presence of either 1 μM oCRF or 100 nM sauvagine. Reactions were terminated by rapid filtration onto Whatman GF/C filters (Brandel) soaked with 0.1% polyethylenimine by use of a 48-well cell harvester (Brandel). Filters were washed three times with ice-cold wash buffer containing: 50 mM $NaPO_4$(pH 7.4), 0.9% NaCl, 2 mM $MgCl_2$, 0.02% $NaN_3$ and 0.01% Triton X-100. Filters were counted on a Packard Cobra gamma counter.

EXAMPLE 33

Cyclic AMP Determination

Approximately two million 293-EBNA Cells/tube expressing either $CRF_1$ or $CRF_{2b}$ receptors were incubated in triplicate at 37° C. in a shaking water bath for ten min in cAMP generation buffer containing: 10 mM HEPES (pH 7.4), 30 mM NaCl, 4.7 mM KCl, 2.5 mM $NaH_2PO_4$, 1.4 mM $MgCl_2$, 1 mM EGTA, 3 mM Glucose, 0.2% BSA and 50 μM 1-methyl-3-isobutylxanthine (IBMX). Cells then were incubated in suspension at 37° C. in siliconized glass 12×75 mm tubes containing various concentrations of antagonists for 25 min. Compounds were first dissolved in 100% DMSO and were further diluted in cAMP generation buffer to yield final concentrations between 1 pM and 100 μM in 1% DMSO. Cells were then stimulated for five min with either 1 nM or 3 nM oCRF (found to be half-maximal for $CRF_1$ or $CRF_{2b}$ receptors, respectively) for cells containing $CRF_1$ or $CRF_{2b}$ receptors, respectively. In order to test for agonist activity, compounds were tested alone or in the presence of forskolin (1–10 μM) for their ability to stimulate cAMP formation. Reactions were stopped by immediately centrifuging the cells 3 min at 500×g. Cell pellets were lysed with 0.5 ml of 0.1N HCl, bath sonicated and centrifuged at 2000×g. Supernatants were transferred to clean glass 12×75 mm test tubes and centrifuged in a Speed-Vac under high heat for 2 h. Dried cell extracts were reconstituted with sodium acetate buffer (pH 6.2, supplied with kit) and analyzed for cAMP by use of a RIA kit (DuPont-New England Nuclear).

EXAMPLE 34

Assessment of in vivo Biological Activity

A variety of in vivo techniques can be utilized for assessment of biological activity. These include and are not limited by: the Acoustic Startle Assay, Cold Swim, physical restraint, ether inhalation, Elevated Plus-maze Test, Stair climbing test, stress- and drug-induced anorexia or Chronic Administration Test as outlined (Heinrichs et al., Ann NY Acad Sci 771:92–104, 1995; Berridge and Dunn, Brain Res Rev 15:71, 1990.). These tests can be performed on rodents and small animals.

EXAMPLE 35

Data Analysis

Binding and functional cAMP data were analyzed with Prism™ (GraphPad, San Diego, Calif.), a computer graphics and statistics program. $IC_50$ values and Hill slopes for radioligand binding experiments were generated by nonlinear regression using Prism™.

What is claimed is:

1. A compound having the structure

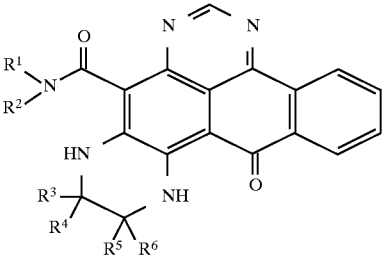

wherein:

$R^1$ and $R^2$ taken together with the nitrogen atom to which they are bonded form an amine, mono- or di-alkylamine, aminoalkylamine, amino alkyl cycloalkyl alkyl amine, or aminocycloalkylamine group;

$R^3$ and $R^6$ are each H;

$R^4$ and $R^5$ are each H, or taken together with the carbon atoms to which they are bonded form a cyclohexyl group;

or an enantiomer or stereoisomer of said compound, or a pharmaceutically acceptable salt of said compound, said enantiomer, or said stereoisomer.

2. A compound according to claim 1 wherein $R^1$ and $R^2$ taken together with the nitrogen atom to which they are bonded form an amine, 2-aminoethylamine, or 1,3-cyclohexyl-bis(methylamine) group;

or an enantiomer or stereoisomer of said compound, or a pharmaceutically acceptable salt of said compound, said enantiomer, or said stereoisomer.

3. A compound according to claim 1 having the structure

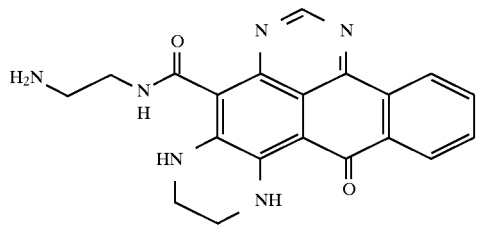

or an enantiomer or stereoisomer of said compound, or a pharmaceutically acceptable salt of said compound, said enantiomer, or said stereoisomer.

4. A compound according to claim 1 having the structure

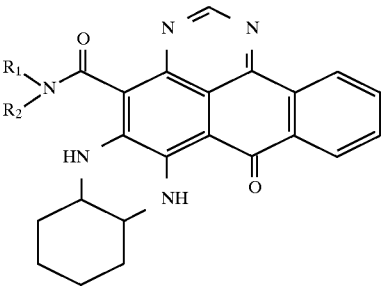

or an enantiomer or stereoisomer of said compound, or a pharmaceutically acceptable salt of said compound, said enantiomer, or said stereoisomer.

5. A compound according to claim 4 having the structure

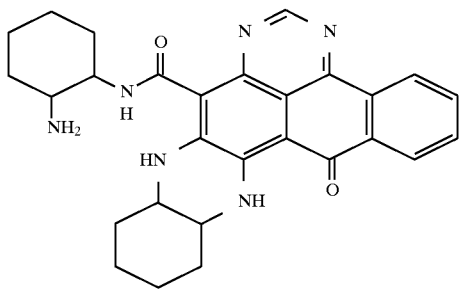

or an enantiomer or stereoisomer of said compound, or a pharmaceutically acceptable salt of said compound, said enantiomer, or said stereoisomer.

6. A compound according to claim 5 having the structure

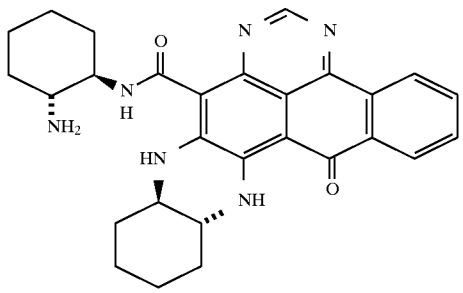

or a pharmaceutically acceptable salt of said compound.

7. A compound according to claim 5 having the structure

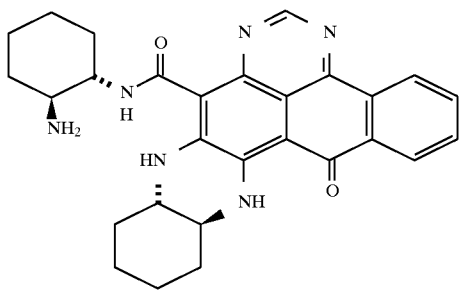

or a pharmaceutically acceptable salt of said compound.

8. A compound according to claim 5 having the structure

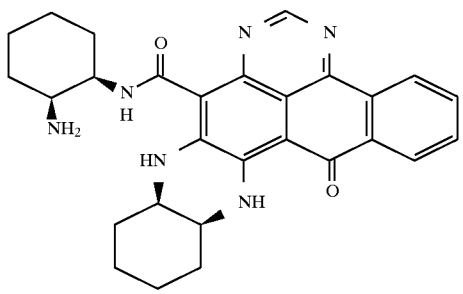

or a pharmaceutically acceptable salt of said compound.

9. A compound according to claim 5 having the structure

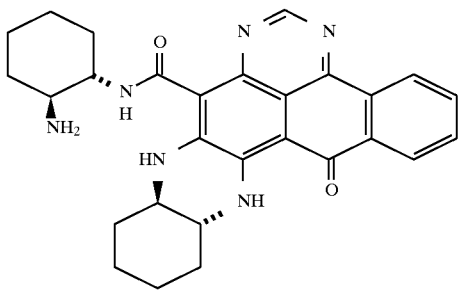

or a pharmaceutically acceptable salt of said compound.

10. A compound according to claim 5 having the structure

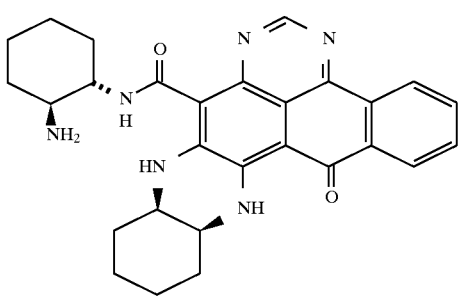

or a pharmaceutically acceptable salt of said compound.

11. A compound according to claim 5 having the structure

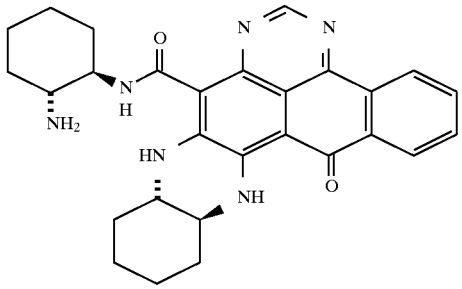

or a pharmaceutically acceptable salt of said compound.

12. A compound according to claim 5 having the structure

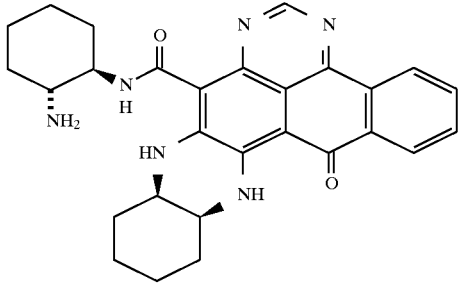

or a pharmaceutically acceptable salt of said compound.

13. A compound according to claim 5 having the structure

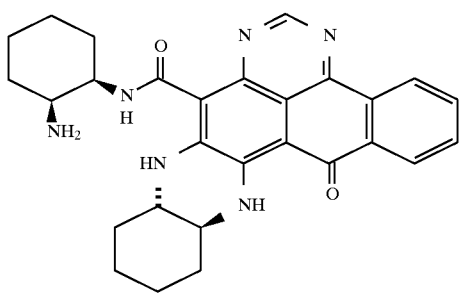

or a pharmaceutically acceptable salt of said compound.

14. A compound according to claim 5 having the structure

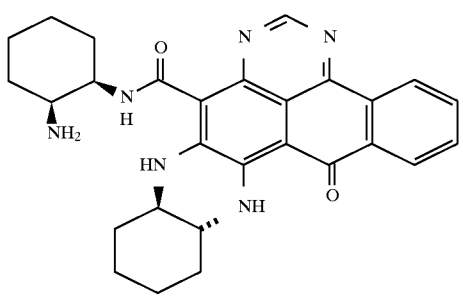

or a pharmaceutically acceptable salt of said compound.

15. A compound according to claim 1 having the structure

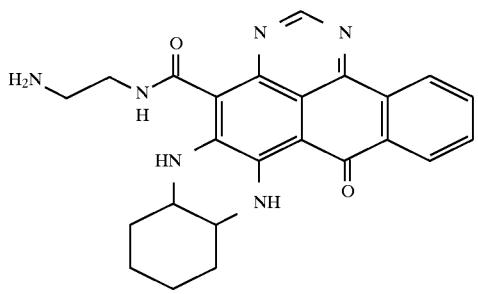

or an enantiomer or stereoisomer of said compound, or a pharmaceutically acceptable salt of said compound, said enantiomer, or said stereoisomer.

16. A compound according to claim 15 having the structure

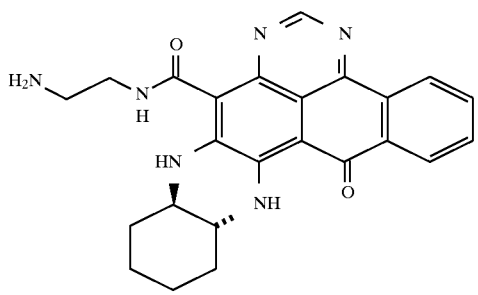

or a pharmaceutically acceptable salt of said compound.

17. A compound according to claim 15 having the structure

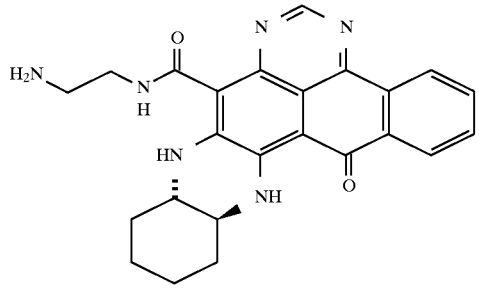

or a pharmaceutically acceptable salt of said compound.

18. A compound according to claim 15 having the structure

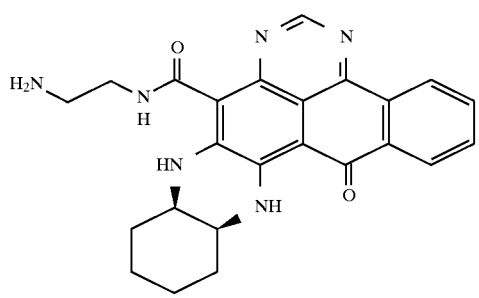

or a pharmaceutically acceptable salt of said compound.

19. A compound according to claim 1 having the structure

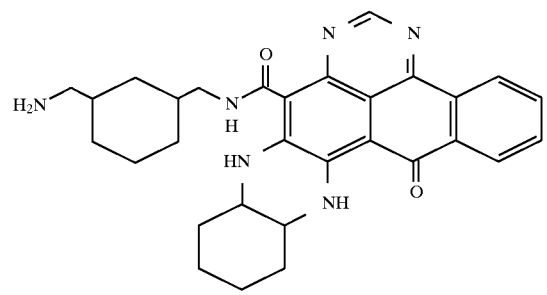

or an enantiomer or stereoisomer of said compound, or a pharmaceutically acceptable salt of said compound, said enantiomer, or said stereoisomer.

20. A compound according to claim 19 having the structure

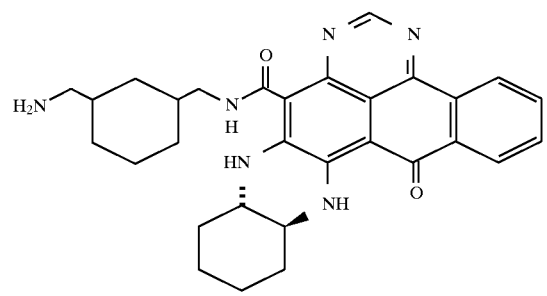

or a pharmaceutically acceptable salt of said compound.

21. A compound according to claim 19 having the structure

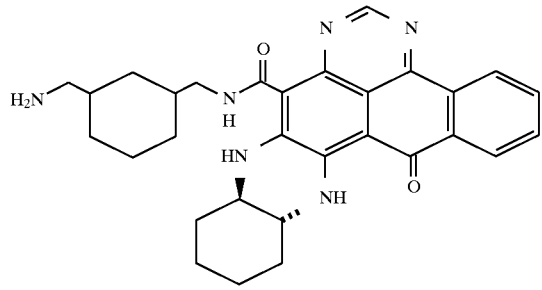

or a pharmaceutically acceptable salt of said compound.

22. A corticotropin releasing factor antagonist pharmaceutical formulation comprising:

(a) a therapeutically effective CRF antagonist amount of a compound, enantiomer, stereoisomer or pharmaceutically acceptable salt of claim 1; and (b) a pharmaceutically acceptable carrier or diluent therefor.

23. A method for blocking the physiological effects of corticotropin releasing factor in a mammal having a CRF-related disorder which comprises administering to said mammal a therapeutically effective CRF-antagonizing amount of any compound, enantiomer, or stereoisomer or pharmaceutically acceptable salt of claim 1.

* * * * *